United States Patent
Gubisch et al.

(10) Patent No.: US 12,017,988 B2
(45) Date of Patent: Jun. 25, 2024

(54) PROCESS FOR DISCHARGING LOW BOILERS DURING THE PRODUCTION OF DIALKYL TEREPHTHALATES OR DIALKYL PHTHALATES

(71) Applicant: Evonik Oxeno GmbH & Co. KG, Marl (DE)

(72) Inventors: Dietmar Gubisch, Dorsten Rhade (DE); Ralf Klaus Hinsken, Dorsten (DE); Johannes Kraft, Niederkassel (DE); Thomas Schneider, Schermbeck (DE)

(73) Assignee: Evonik Oxeno GmbH & Co. KG, Marl (DE)

( * ) Notice: Subject to any disclaimer, the term of this patent is extended or adjusted under 35 U.S.C. 154(b) by 251 days.

(21) Appl. No.: 17/804,015

(22) Filed: May 25, 2022

(65) Prior Publication Data

US 2022/0380294 A1     Dec. 1, 2022

(30) Foreign Application Priority Data

May 28, 2021 (EP) ..................................... 21176570

(51) Int. Cl.
*C07C 67/54* (2006.01)
(52) U.S. Cl.
CPC .................................. *C07C 67/54* (2013.01)
(58) Field of Classification Search
CPC ......... C07C 67/54; C07C 67/03; C07C 67/08; C07C 69/80; C07C 69/82; C07C 67/29; C07C 69/76
See application file for complete search history.

(56) References Cited

U.S. PATENT DOCUMENTS

| | | |
|---|---|---|
| 10,544,279 B2 | 1/2020 | Boeck et al. |
| 2004/0238787 A1 | 12/2004 | Wiese et al. |
| 2010/0305255 A1 | 12/2010 | Grass |
| 2016/0237244 A1 | 8/2016 | Boeck et al. |
| 2022/0033618 A1 | 2/2022 | Kraft et al. |

FOREIGN PATENT DOCUMENTS

| | | |
|---|---|---|
| EP | 1 719 753 | 11/2006 |
| EP | 3 059 222 | 8/2016 |
| EP | 3 059 223 | 8/2016 |
| WO | 2009/095126 | 8/2009 |
| WO | 03/029180 | 4/2023 |

OTHER PUBLICATIONS

Extended European Search Report dated Nov. 19, 2021 in European Patent Application No. 21176570.6, 6 pages.
U.S. Appl. No. 17/385,323, filed Jul. 26, 2020, 2022/0033618, Kraft et al.
Zanthoff et al., U.S. Appl. No. 17/931,559 dated Sep. 13, 2022.
U.S. Appl. No. 17/931,559, filed Sep. 13, 2022, Zanthoff et al.

*Primary Examiner* — Deborah D Carr
(74) *Attorney, Agent, or Firm* — Grüneberg and Myers PLLC

(57) ABSTRACT

A process discharges low boilers during production of dialkyl terephthalates or dialkyl phthalates having C8 to C11 alkyl radicals. The production is carried out using a C8 to C11 alcohol or a mixture of two or more C8 to C11 alcohols in one or more reactors. The low boilers formed during the reaction are separated off by an efficient process and thus cannot accumulate.

13 Claims, No Drawings

PROCESS FOR DISCHARGING LOW BOILERS DURING THE PRODUCTION OF DIALKYL TEREPHTHALATES OR DIALKYL PHTHALATES

CROSS-REFERENCE TO RELATED APPLICATION

This application claims the benefit to European Application No. 21176570.6, filed on May 28, 2021. The content of this application is hereby incorporated by reference in its entirety.

BACKGROUND

Field of the Invention

The present invention relates to a process for discharging low boilers during the production of dialkyl terephthalates or dialkyl phthalates having C8 to C11 alkyl radicals, wherein the production is carried out using a C8 to C11 alcohol or a mixture of two or more C8 to C11 alcohols in one or more reactors. The low boilers formed during the reaction, for example alkenes obtained by elimination or water from the alcohols, are separated off by an efficient process and thus cannot accumulate.

Description of the Related Art

Dialkyl terephthalates or dialkyl phthalates have been produced for many years using processes known in the prior art. Direct esterification of terephthalic acid or of phthalic acid, or of the corresponding acid anhydride, with the respective alcohol or a mixture of multiple alcohols is of particular industrial significance in this case. The latter leads to mixed esters, in which the two ester groups may bear different alkyl radicals. A further known way of producing dialkyl terephthalates or dialkyl phthalates is transesterification of dimethyl phthalate or dimethyl terephthalate with the respective alcohol. Both processes, i.e. both esterification and transesterification, and the conditions necessary therefor are known to those skilled in the art, for example from the patent applications WO 03/029180 A1, WO 2009/095128 A1, EP 3 059 222 A1 and EP 3 059 223 A1.

However, it is frequently not only the desired products that are formed during the production of dialkyl terephthalates or dialkyl phthalates. By-products may also form, for example alkenes by elimination of water from the alcohols used. Occasionally these alkenes may lead to discolorations and odour formation, and are therefore undesirable. These by-products collect in the reaction mixture and would be obtained together with the unconverted alcohols during the product separation, that is to say accumulate therein. The alcohol separated from the reaction mixture or the alcohol mixture separated from the reaction mixture can, and should, be reused in subsequent esterifications or transesterifications, not least for economic reasons. However, the separated alcohol or the separated alcohol mixture has to be completely discarded in the case of an excessively high concentration of by-products, so as not to cause any consequential problems in the esterification or transesterification.

SUMMARY

The object of the present invention was therefore that of providing a process with which the low boilers can be discharged in a simple manner, without having to discard large amounts of the separated alcohol or of the separated alcohol mixture. A further object was that of providing a process that does not require great apparatus construction, but instead can be very easily integrated even into existing plants.

The underlying object of the present invention was achieved by the process described here for discharging low boilers during the production of dialkyl terephthalates having C8 to C11 alkyl radicals or dialkyl phthalates having C8 to C11 alkyl radicals. The corresponding process is described in embodiments disclosed herein.

The present invention therefore provides a process for discharging low boilers during the production or dialkyl terephthalates having C8 to C11 alkyl radicals or dialkyl phthalates having C8 to C11 alkyl radicals, wherein the production is carried out in each case using a C8 to C11 alcohol or a mixture or two or more C8 to C11 alcohols in one or more reactors, wherein, once a conversion of at least 90%, preferably at least 92%, particularly preferably at least 95%, has been reached during the production of the dialkyl terephthalates or dialkyl phthalates, a slightly reduced pressure in the range from 400 to 900 mbar absolute is generated in the reactor or reactors, as a result of which a low-boiler phase of the reaction mixture comprising at least unconverted alcohol and reaction by-products is distilled off, wherein the first portion of the low-boiler phase distilled off is discharged, the amount of the discharged portion of the low-boiler phase being 0.05% to 8% by weight, preferably 0.1% to 4% by weight, of the entire distilled-off low-boiler phase.

The inventive advantage of this process is the straightforward configuration that does not require any particular complexity in terms of preparation or apparatus. It is possible without difficulty to discharge and hence discard the first portion distilled over in existing plants once the reduced pressure has been applied. There is therefore no need for an additional distillation column for work-up of the unconverted alcohol after separation from the reaction mixture. It is clear that, in the process according to the invention, a portion of the unconverted alcohol or of the unconverted alcohol mixture is also present in the first portion of the low-boiler phase distilled over and is correspondingly likewise discarded. This is negligible when considering the apparatus construction otherwise necessary with an additional distillation column or the discarding of the complete low-boiler phase in the case of an excessively high concentration of by-products.

DETAILED DESCRIPTION OF THE INVENTION

The process according to the invention comprises the production of dialkyl terephthalates having C8 to C11 alkyl radicals or dialkyl phthalates having C8 to C11 alkyl radicals. This is accomplished in particular by esterification of terephthalic acid or phthalic acid or phthalic anhydride, or by transesterification of dimethyl phthalate or dimethyl terephthalate. Both processes involve the use of C8 to C11 alcohols or a mixture of two or more C8 to C11 alcohols in order to produce the corresponding esters or mixed esters.

Esterification of terephthalic acid or terephthalic anhydride, or of phthalic acid or phthalic anhydride, with C8 to C11 alcohols or a mixture of two or more C8 to C11 alcohols is a known process and is already described in the prior art, for example in WO 03/029180 A1 or WO 2009/095126 A1.

Esterification usually takes place in the liquid phase. Here, the corresponding acid or the corresponding acid anhydride is reacted with the respective alcohol or the respective alcohol mixture in the presence of a suitable catalyst, with water being formed. The water formed during the esterification is preferably separated off even while the reaction is ongoing. Since the reaction temperatures are usually above the boning point of water, the water or an azeotrope of water and alcohol can easily be separated off in vaporous form. Phthalic acid or phthalic anhydride is preferably used in the esterification process according to the Invention.

Transesterification of dimethyl phthalate or dimethyl terephthalate with C8 to C11 alcohols or a mixture of two or more C8 to C11 alcohols is likewise a known process and is already described in the prior art, for example in WO 2009/095128 A1. Transesterification usually takes place in the liquid phase. This involves reacting the dimethyl phthalate or dimethyl terephthalate with the respective alcohol or the respective alcohol mixtures in the presence of a suitable catalyst. This replaces the methoxy group of dimethyl phthalate or dimethyl terephthalate with an alkoxy group that corresponds to the alcohol used or to an alcohol of the alcohol mixture with respect to the carbon number, forming methanol. The methanol formed during the transesterification is preferably separated off even while the reaction is ongoing. Since the reaction temperatures are usually above the boiling point of methanol, the methanol can easily be separated off in vaporous form. Dimethyl terephthalate is used with preference in the transesterification process according to the invention.

The alcohol used in the esterification according to the invention or transesterification according to the invention is a C8 to C11 alcohol or a mixture of two or more C8 to C11 alcohols. This in particular includes 2-ethylhexanol, octanol, isononanol, nonanol, isodecanol, decanol, 2-propylheptanol, undecanol or a mixture of two of these alcohols. Preference is given to using 2-ethylhexanol, isononanol, 2-propylheptanol, or mixtures of C9 and C11 alcohols in the context of this invention. Particular preference is given to using isononanol, 2-propylheptanol or isodecanol in the esterification according to the Invention or transesterification according to the Invention.

The esterification according to the invention or transesterification according to the invention is preferably performed batchwise. The batchwise mode of operation preferred in this case is in particular a batch production. An amount limited by the reactor volume is thus produced and then the reaction is ended. A new batch production can subsequently be started after the reactor has been emptied.

Suitable reactors are reactors known to those skilled in the art that can be used for the synthesis of dialkyl terephthalates having C8 to C11 alkyl radicals or dialkyl phthalates having C8 to C11 alkyl radicals. Suitable reactors in particular comprise a distillation column, via which the water formed or the methanol formed and, after the reaction, also the unconverted alcohols are separated off. The distillation column is preferably fixedly connected to the reactor or the reactors of the process according to the invention. The reactor then effectively constitutes the bottom of the distillation column. The prevailing reaction temperatures make it possible for water or methanol to be converted to the gas phase even while the esterification or the transesterification is ongoing and be distilled off via the distillation column. The amount of liquid lost as a result can be replaced by means of supply of the alcohol used or of the alcohol mixture used.

The temperature during the production of dialkyl terephthalates having C8 to C11 alkyl radicals or dialkyl phthalates having C8 to C11 alkyl radicals depends on various factors, for example on the reaction variant performed, but is preferably from 150° C. to 260° C. This temperature range is suitable both for esterification and for transesterification. The pressure during esterification and transesterification is preferably in the range from 0.5 to 10 bar absolute. The temperature and pressure should preferably be set such that the water formed or the methanol formed can be distilled off even while the reaction is ongoing.

At the end or the reaction, the produced dialkyl terephthalates having C8 to C11 alkyl radicals or dialkyl phthalates having C8 to C11 alkyl radicals are present in a reaction solution which also comprises, in addition to the produced compounds, at least the unconverted alcohols or the unconverted alcohol mixture. As already outlined, by-products that have a lower boiling point than the alcohols or alcohol mixtures used may form during the esterification or the transesterification. The most important by-products are alkenes formed by the elimination of water from the alcohol used. In the case of the alcohols used here, the respective alkenes always have a lower boiling point than the respective alcohols from which the alkene has formed.

The by-products that have formed are present in the reaction solution with the produced dialkyl terephthalates having C8 to C11 alkyl radicals or dialkyl phthalates having C8 to C11 alkyl radicals and the unconverted alcohols. After the reaction the unconverted alcohols are separated from the reaction product that has formed, which leaves the formed dialkyl terephthalates having C8 to C11 alkyl radicals or dialkyl phthalates having C8 to C11 alkyl radicals as the crude product. The by-products that have formed are thus separated together with the unconverted alcohols from the reaction product that has formed, since said by-products, as mentioned, generally have a lower boiling point. The low-boiler phase separated off for generation of the crude product consequently comprises at least the unconverted alcohols and the by-products that have formed.

The unconverted alcohols, or the separated low-boiler phase, are usually used in a subsequent production of dialkyl phthalates or dialkyl terephthalates, which is why the by-products would build up if they were not separated. Since the alkenes in particular are highly-reactive molecules, they can cause problems in the subsequent productions, especially if they build up further and further. Associated problems are worsened odour and/or worsened colouration.

The solution according to the invention is to discharge a portion of a low-boiler phase that is distilled off by application of a slightly reduced pressure of 400 to 900 mbar absolute, preferably 500 to 800 mbar absolute. The reduced pressure is not applied arbitrarily, however, but rather only once a threshold value has been reached, here the reaction conversion. The reduced pressure mentioned or 400 to 900 mbar absolute, preferably 500 to 800 mbar absolute, is applied after a conversion of at least 90%, preferably of at least 92%, especially preferably of at least 95%, has been reached, in particular for up to one hour once said conversion has been reached. It would be possible to monitor the conversion for this purpose even while the reaction is ongoing. Alternatively it is possible for not the conversion but just one other parameter or multiple other parameters to be monitored during the reaction, with the parameter(s), possibly after prior calibration, allowing a conclusion to be drawn regarding the conversion or, more generally, the progress of the reaction. An example would be monitoring of the reaction temperature or of the temperature of the reaction mixture, with the reduced pressure being applied once a particular temperature has been reached, possibly after a particular time interval has elapsed. Monitoring of the reaction progress by means of gas chromatography, by means of online analysis (e.g., Infrared spectroscopy) or on the basis of the acid number would alternatively be conceivable. It would alternatively be possible to apply the desired reduced pressure after a previously determined reaction time. It should be pointed out here that the proposed solution does not preclude the reaction from still continuing up to a virtually complete or complete conversion while the reduced pressure is applied.

The slightly reduced pressure of 400 to 900 mbar absolute is applied in the reactor as soon as the stated threshold value is reached. This can be achieved by means of known apparatuses or machines. A (vacuum) pump which generates the reduced pressure in the reactor is an example of such a suitable apparatus. The temperature when the reduced pressure is applied may correspond to the reaction temperature. If the reduced pressure is only applied with a certain delay once the threshold value for the conversion has been reached, the temperature may also be lower than the reaction temperature.

The slightly reduced pressure applied causes the evaporation of at least portions of the low-boiling components, that is to say the low-boiling by-products, but only a minor degree of evaporation of the unconverted alcohols or the unconverted alcohol mixture, and they are obtained as low-boiler phase. This low-boiler phase is then distilled off. Since the low-boning by-products generally have a lower boning point than the unconverted alcohols, initially, once the slightly reduced pressure has been applied, the low-boiler phase will comprise predominately these by-products. The first portion of the low-boiler phase distilled over when the low-boiler phase is distilled off, that is to say the first portion of the low-boiler phase distilled off once the reduced pressure has been applied, is therefore discharged and discarded. The amount of the discharged portion of the low-boiler phase is 0.05% to 8% by weight, preferably 0.1% to 4% by weight, based on the amount of the entire distilled-off low-boiler phase separated off for generation of the crude product. It cannot be ruled out that unconverted alcohols will also be lost during the discharging, this being accepted in light of the advantages of the process.

The first portion of the low-boiler phase distilled over can be discharged with a low degree of apparatus complexity, for example using a suitable valve. The amount of the discharged portion of the low-boiler phase can then be measured using a suitable flow meter and the discharging of the desired amount can be ended, for example by closing the valve. The discharged low-boiler phase, after the discharging, can be dewatered and subsequently utilized physically or thermally.

Once the first portion of the low-boiler phase distilled over has been discharged, the distillation is continued in order to distil off the remaining low-boiler phase and to generate the crude product. The low-boiler phase that is distilled over during the distillation is then condensed, collected in a suitable vessel and sent to a water separator in order to separate off any water that may still be present. The liquid low-boiler phase, which at this point virtually exclusively contains unconverted alcohols, is then stored in a vessel and may be used in a subsequent process for the production of dialkyl terephthalates having C8 to C11 alkyl radicals or dialkyl phthalates having C8 to C11 alkyl radicals. Due to the reduced pressure applied, the temperature may decrease while the low-boiler phase is being separated off, especially once the reaction has ended completely.

In a preferred embodiment of the present invention, the pressure is reduced further once the first portion of the low-boiler phase distilled over has been discharged. The removal of the low-boiler phase, which then consists predominately of the unconverted alcohols, can thus be accelerated. The pressure is preferably lowered here to 30 to 300 mbar absolute, preferably 50 to 200 mbar absolute. The same applies to the temperature in this case as described above. i.e. the temperature will preferably decrease with time while the low-boiler phase is being separated off.

In a preferred embodiment of the present invention, the discharging process according to the invention is used in the production of a dialkyl terephthalate or a dialkyl phthalate from the group consisting of diisononyl phthalate (DINP), di(2-propylheptyl) phthalate (DPHP), diisodecyl phthalate (DIDP), diisononyl terephthalate (DINT) and di(2-ethylhexyl) terephthalate (DOTP). In a particularly preferred embodiment, the process is used in the production of diisononyl phthalate (DINP). The invention then provides a process for discharging low boilers during the production of diisononyl phthalate (DINP) by esterification or phthalic acid or phthalic anhydride with isononanol (INA) or by transesterification of dimethyl phthalate (DMT) with isononanol in one or more reactors, wherein, once a conversion of least 90%, preferably at least 92%, particularly preferably at least 95%, has been reached during the production of DINP, a slightly reduced pressure in the range from 400 to 900 mbar absolute is generated in the reactor or reactors, as a result of which a low-boiler phase of the reaction mixture comprising at least unconverted isononanol and reaction by-products is distilled off, characterized in that the first portion of the low-boiler phase distilled off is discharged, the amount or the discharged portion of the low-boiler phase being 0.05% to 8% by weight, preferably 0.1% to 4% by weight, or the entire distilled-off low-boiler phase.

The reaction by-products in this case may be nonenes formed by elimination of water from isononanol. Nonenes and isononanol can be separated from one another quite easily by means of a sufficiently large distillation column, which is why it is possible here, under some circumstances, for the proportion of alcohol in the discharged low-boiler phase to be kept low.

The dialkyl terephthalates having C8 to C11 alkyl radicals or dialkyl phthalates having C8 to C11 alkyl radicals, in the production of which the process according to the invention is used, may advantageously be employed as plasticizers or as a component of a plasticizer composition in plastics or plastic compositions, as an additive in paints or varnishes, in adhesives or adhesive components, in sealants or as solvents.

The dialkyl terephthalates having C8 to C11 alkyl radicals or dialkyl phthalates having C8 to C11 alkyl radicals may also be employed as plasticizers in mixtures with other plasticizers, in particular what are known as fast gelators. Examples of such other plasticizers are dialkyl terephthalates or dialkyl phthalates having alkyl radials with fewer than 8 carbon atoms, trialkyl trimellitates or glycol benzoates, and also citrates or C8-C10 monoalkyl benzoates. The proportion of the dialkyl terephthalates having C8 to C11 alkyl radicals or dialkyl phthalates having C8 to C11 alkyl radicals is then preferably 15% to 95% by weight, particularly preferably 20% to 90% by weight and very particularly preferably 25% to 85% by weight, the proportions of all plasticizers present adding up to 100% by weight. The above compositions composed of the dialkyl terephthalates having C8 to C11 alkyl radicals or dialkyl phthalates having C8 to C11 alkyl radicals and other plasticizers may be employed as a plasticizer composition in plastics and plastic compositions, adhesives, sealants, varnishes, paints, plastisols or inks.

The plastic compositions that may comprise the dialkyl terephthalates having C8 to C11 alkyl radicals or dialkyl phthalates having C8 to C11 alkyl radicals may comprise polymers selected from polyvinyl chloride (PVC), polyvinylidene chloride (PVDC), polyacrylates, in particular polymethyl methacrylate (PMMA), polyalkyl methacrylate (PAMA), fluoropolymers, in particular polyvinylidene fluoride (PVDF), polytetrafluoroethylene (PTFE), polyvinyl acetate (PVAc), polyvinyl alcohol (PVA), polyvinyl acetals, in particular polyvinyl butyral (PVB), polystyrene polymers, in particular polystyrene (PS), expandable polystyrene (EPS), acrylonitrile-styrene-acrylate (ASA), styrene-acrylonitrile (SAN), acrylonitrile-butadiene-styrene (ABS), styrene-maleic anhydride copolymer (SMA), styrene-methacrylic acid copolymer, polyolefins, in particular polyethylene (PE) or polypropylene (PP), thermoplastic polyolefins (TPO), polyethylene-vinyl acetate (EVA), polycarbonates, polyethylene terephthalate (PET), polybutylene terephthalate (PBT), polyoxymethylene (POM), polyamide (PA), polyethylene glycol (PEG), polyurethane (PU), thermoplastic polyurethane (TPU), polysulfides (PSu), biopolymers, in particular polylactic acid (PLA), polyhydroxybutyric acid (PHB), polyhydroxyvaleric acid (PHV), polyesters, starch, cellulose and cellulose derivatives, in particular nitrocellulose (NC), ethylcellulose (EC), cellulose acetate (CA), cellulose acetate/butyrate (CAB), rubber or silicones, and mixtures or copolymers of the above polymers or of the monomeric units thereof. The compositions according to the invention preferably include PVC or homo- or copolymers based on ethylene, propylene, butadiene, vinyl acetate, glycidyl acrylate, glycidyl methacrylate, methacrylates, acrylates, acrylates or methacrylates with alkyl radicals, bonded to the oxygen atom of the ester group, of branched or unbranched alcohols having one to ten carbon atom(s), styrene, acrylonitrile or cyclic olefins. Particular preference is given to the use of PVC.

The type of PVC present in the plastic composition according to the invention is preferably suspension PVC, bulk PVC, microsuspension PVC or emulsion PVC. The compositions according to the invention preferably comprise from 5 to 200, more preferably from 10 to 150, parts by weight of plasticizer according to the invention based on 100 parts by weight of polymer.

In addition to the above constituents, the plastic compositions may comprise further constituents, in particular, for example, further plasticizers, filers, pigments, stabilizers, co-stabilizers such as epoxidized soybean oi, lubricants, blowing agents, kickers, antioxidants, rheology additives, light stabilizers or biocides.

The plastic compositions according to the invention composed of the dialkyl terephthalates having C8 to C11 alkyl radicals or dialkyl phthalates having C8 to C11 alkyl radicals and the aforementioned polymer materials may be employed as plastic compositions, adhesives, sealants, varnishes, paints, plastisols, imitation leather, floor coverings, underbody protection, fabric coatings, roof membranes, wallpaper or inks or for the production thereof.

Plastic products produced with the plasticizer compositions may for example be profiles, seals, food packaging, films, toys, medical items, roof sheeting. Imitation leather, floor coverings, underbody protection, coated fabrics, roof membranes, wallpaper, cabling and wire sheathing. Preferred fields of use from this group are food packaging, toys, medical items, wallpaper, roof membranes, fabric coatings and floor coverings.

The invention claimed is:

1. A process for discharging low boilers during production of dialkyl terephthalates having C8 to C11 alkyl radicals or dialkyl phthalates having C8 to C11 alkyl radicals, wherein the production is carried out in each case using a C8 to C11 alcohol or a mixture of two or more C8 to C11 alcohols in one or more reactors, the process comprising:
    after a conversion of at least 90% has been reached during the production of the dialkyl terephthalates or dialkyl phthalates, reducing pressure to be in a range from 400 to 900 mbar absolute in the one or more reactors, wherein a low-boiler phase of a reaction mixture comprising at least unconverted alcohol and reaction by-products is distilled off, and
    discharging a first portion of the low-boiler phase that is distilled off, an amount of the discharged first portion of the low-boiler phase being 0.05% to 8% by weight of an entire distilled-off low-boiler phase.

2. The process according to claim 1, wherein the pressure is reduced at a conversion of at least 92%.

3. The process according to claim 1, wherein the pressure is reduced at a conversion of at least 95%.

4. The process according to claim 1, wherein the pressure is reduced for up to one hour once the conversion has been reached.

5. The process according to claim 1, wherein the amount of the discharged first portion of the low-boiler phase is 0.1% to 4% by weight of the entire distilled-off low-boiler phase.

6. The process according to claim 1, wherein the reaction by-products comprise alkenes formed by elimination of water from the C8 to C11 alcohol or the mixture of two or more C8 to C11 alcohols used.

7. The process according to claim 1, wherein the reactor or reactors comprise a distillation column.

8. The process according to claim 1, wherein a remaining low-boiler phase comprising the at least unconverted alcohol is distilled off once the first portion of the low-boiler phase distilled over has been discharged.

9. The process according to claim 8, wherein the pressure is reduced further while the remaining low-boiler phase is distilled off.

10. The process according to claim 9, wherein the pressure after being further reduced is 30 to 300 mbar absolute.

11. The process according to claim 9, wherein the distilled-off remaining low-boiler phase is used in a subsequent process for production of dialkyl terephthalates having C8 to C11 alkyl radicals or dialkyl phthalates having C8 to C11 alkyl radicals.

12. The process according to claim 1, wherein the dialkyl terephthalate or the dialkyl phthalate is selected from the group consisting of diisononyl phthalate (DINP), di(2-propylheptyl) phthalate (DPHP), diisodecyl phthalate (DIDP), diisononyl terephthalate (DINT), and di(2-ethylhexyl) terephthalate (DOTP).

13. A process for discharging low boilers during production of diisononyl phthalate (DINP) by esterification of phthalic acid or phthalic anhydride with isononanol (INA) or by transesterification of dimethyl phthalate (DMT) with isononanol in one or more reactors, the process comprising:

after a conversion of at least 90% has been reached during the production of DINP, reducing pressure to be in a range from 400 to 900 mbar absolute in the one or more reactors, wherein a low-boiler phase of a reaction mixture comprising at least unconverted isononanol and reaction by-products is distilled off, and discharging a first portion of the low-boiler phase that is distilled off, an amount of the discharged first portion of the low-boiler phase being 0.05% to 8% by weight of an entire distilled-off low-boiler phase.

\* \* \* \* \*